US008444558B2

(12) United States Patent
Young et al.

(10) Patent No.: US 8,444,558 B2
(45) Date of Patent: *May 21, 2013

(54) APPARATUS FOR MONITORING VITAL SIGNS HAVING FLUID BLADDER BENEATH PADDING

(75) Inventors: Steven J. Young, Los Gatos, CA (US); Richard V. Rifredi, Los Gatos, CA (US); Yuri Zhovnirovsky, Albany, CA (US)

(73) Assignee: BAM Labs, Inc., Campbell, CA (US)

( * ) Notice: Subject to any disclaimer, the term of this patent is extended or adjusted under 35 U.S.C. 154(b) by 998 days.

This patent is subject to a terminal disclaimer.

(21) Appl. No.: 12/349,667

(22) Filed: Jan. 7, 2009

(65) Prior Publication Data

US 2010/0174198 A1 Jul. 8, 2010

(51) Int. Cl.
*A61B 5/00* (2006.01)
*A61B 5/04* (2006.01)
*A61B 5/08* (2006.01)

(52) U.S. Cl.
USPC .......................... 600/301; 600/372; 600/534

(58) Field of Classification Search
None
See application file for complete search history.

(56) References Cited

U.S. PATENT DOCUMENTS

| 5,675,855 | A | * | 10/1997 | Culp ................................. 5/709 |
| 5,684,460 | A | * | 11/1997 | Scanlon ..................... 340/573.1 |
| 6,848,135 | B1 | | 2/2005 | Kohlman |
| 7,330,127 | B2 | * | 2/2008 | Price et al. .................... 340/666 |
| 2005/0022606 | A1 | * | 2/2005 | Partin et al. ..................... 73/773 |
| 2005/0154336 | A1 | | 7/2005 | Kloecker et al. |
| 2008/0060138 | A1 | | 3/2008 | Price et al. |
| 2008/0077020 | A1 | | 3/2008 | Young et al. |

FOREIGN PATENT DOCUMENTS

| JP | 2004-049838 A | 2/2004 |
| JP | 2004-113618 A | 4/2004 |
| JP | 2004-130012 A | 4/2004 |
| JP | 2007-125337 A | 5/2007 |
| JP | 2008-259745 A | 10/2008 |
| JP | 2010-094379 A | 4/2010 |

OTHER PUBLICATIONS

Notification of Transmittal, International Search Report and Written Opinion of the International Searching Authority (ISA/KR) dated Aug. 13, 2010 from the corresponding International Patent Application No. PCT/US2010/020205.

* cited by examiner

*Primary Examiner* — Celine Qian

(74) *Attorney, Agent, or Firm* — Young Basile

(57) ABSTRACT

A sleeping monitoring system includes a first padding layer. A fluid bladder is beneath the first padding layer. A sensor is in fluid communication with the fluid bladder. The sensor is configured to output a vital sign signal.

19 Claims, 4 Drawing Sheets

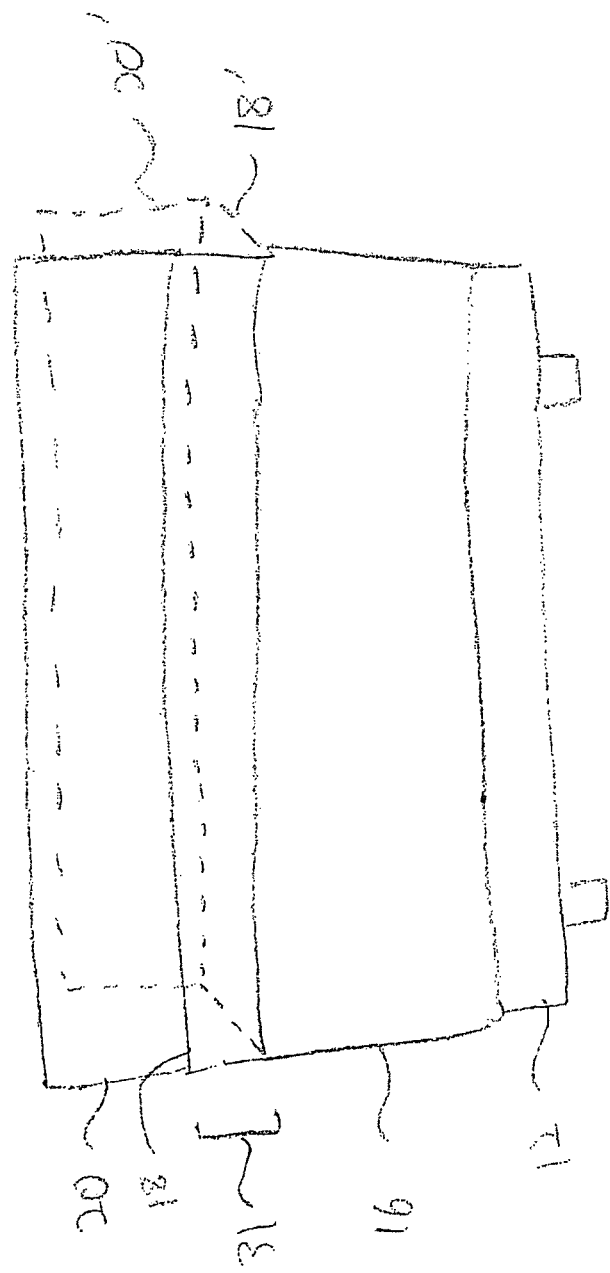

APPARATUS FOR MONITORING VITAL SIGNS HAVING FLUID BLADDER BENEATH PADDING

FIELD OF THE INVENTION

The present invention pertains to a vital sign monitoring apparatus.

BACKGROUND

Historically, monitoring vital signs of a person has required expensive equipment, such as an electrocardiogram (EKG) or a ballistocardiograph (BCG). In addition to being prohibitively expensive for many situations (e.g., home use), both EKGs and BCGs can be too cumbersome for use outside of medical facilities. EKGs, for example, typically necessitate attaching electrodes to the bodies of users, while BCGs rely on large, heavy, and unaesthetic force-measuring platforms that users lie on.

In more recent times, devices including piezoelectric films or arrays of sensors have been developed to measure heart and respiration rates. A user can lie on the device, and the film or sensors can generate a signal indicate of the user's heart rate and/or respiration rate. However, these devices can also be expensive.

SUMMARY

Placing a sensor beneath a padding layer can provide more comfort than having a sensor occupy a top position on a mattress. However, when the sensor is placed beneath the padding layer, the padding layer can dampen pressure input to the mattress, thereby preventing the sensor from properly detecting pressure. For example, if the sensor is near a foot of the mattress and beneath the padding layer, a pressure exerted on the mattress resulting from a heart beat will not likely create a wave in the padding layer of sufficient strength to propagate all the way through the padding layer to the sensor. Using a fluid bladder beneath the padding layer can aid in the transmission of waves resulting from pressure exerting on the padding layer to the sensor.

Accordingly, one example of a sleep monitoring system includes a first padding layer. A fluid bladder is beneath the first padding layer. A sensor is in fluid communication with the fluid bladder, and the sensor is configured to output a vital sign signal.

In another example, a mattress for determining at least one vital sign of a person lying thereon is provided. The mattress includes a first foam layer and a second foam layer. A fluid bladder is between the first and second foam layers, and the fluid bladder defines at least one aperture extending between a top side of the fluid bladder that the first foam layer rests on and a bottom side that rests on the second foam layer. A sensor in fluid communication with the fluid bladder is configured to output a vital sign signal.

BRIEF DESCRIPTION OF THE DRAWINGS

The description herein makes reference to the accompanying drawings, wherein like reference numerals refer to like parts throughout the several views, and wherein:

FIG. 6 is an end view of the mattress of FIG. 1.

DETAILED DESCRIPTION

Figure 1:
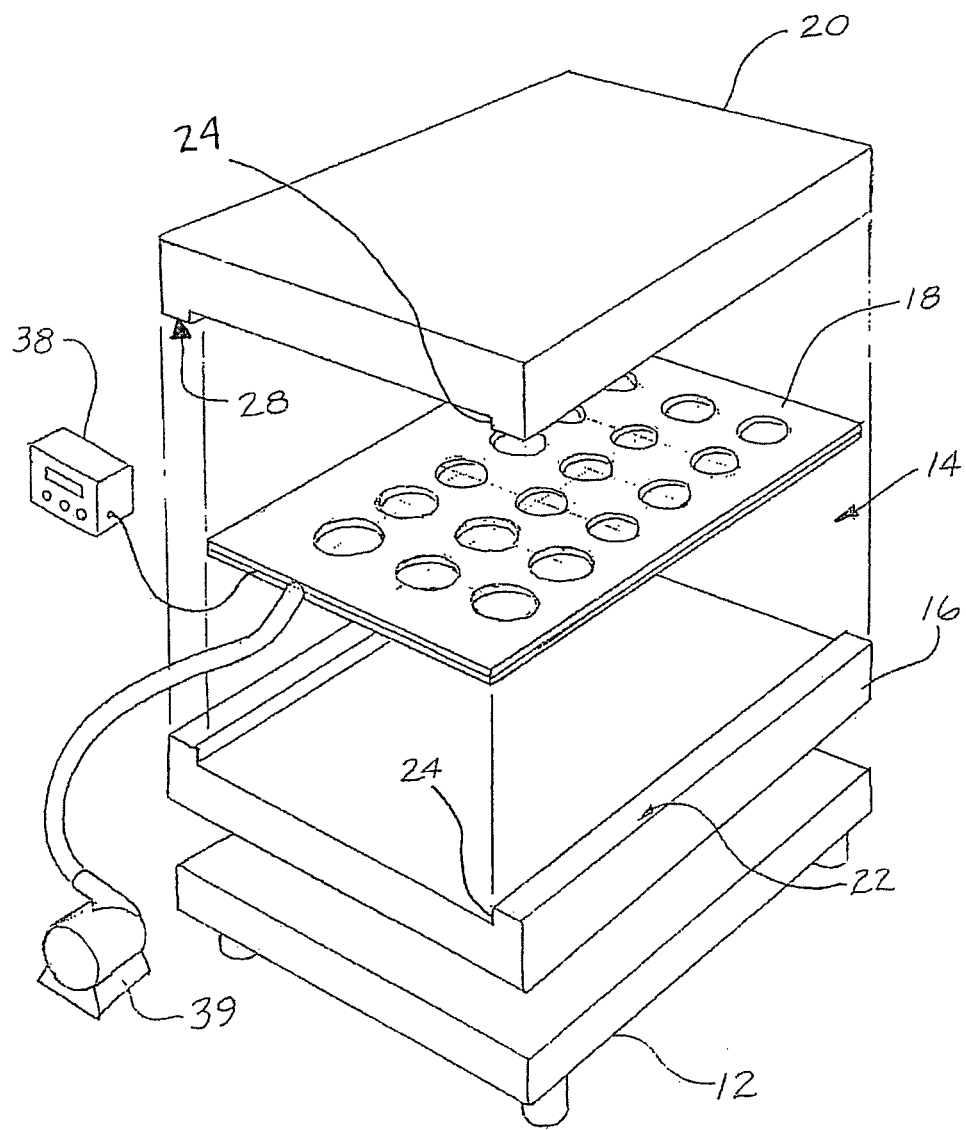
FIG. 1 is an exploded perspective view of an example of a mattress including a sensing layer.
Figure 2:
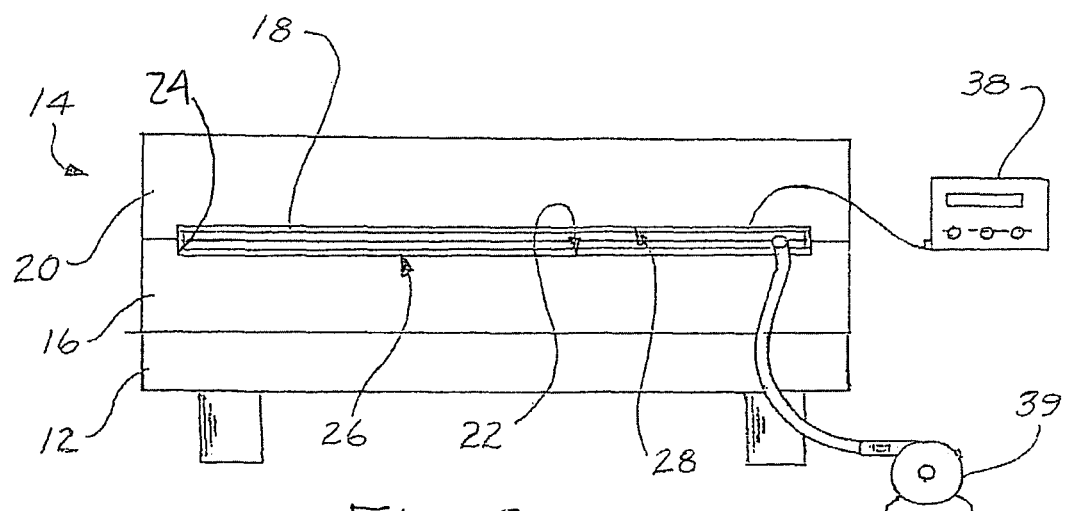
FIG. 2 is an end view of the mattress of FIG. 1.

A bed 10 as shown in FIGS. 1-2 can include a frame 12 and a mattress 14. The frame 12 can be a standard sized bed frame, such as a frame for holding a twin, full, queen, or king mattress. The frame 12 can hold the mattress 14 off the ground, such as at a level allowing a user to easily mount and dismount the mattress 14. While shown as a standard bed frame, the frame 12 can alternatively be a crib, hospital bed, or another support structure for the mattress 14. Also, the mattress 14 can be set directly on the ground or a floor, in which case no frame 12 is necessary.

The mattress 14 can have a standard size (e.g., a twin, full, queen or king size) or be sized for use in a crib, on a hospital bed, or in another environment. The mattress 14 can include a bottom padding layer 16, the sensing layer 18, and a top padding layer 20, with the sensing layer 18 sandwiched between the padding layers 16 and 20 as shown in FIGS. 1 and 2. The mattress 14 can be an integral, inseparable unit, or the mattress 14 can be formed by stacking separate layers 16, 18 and 20.

The bottom padding layer 14 can be a firm layer for providing support. For example, the bottom layer 14 can include firm high density foam (e.g., visco-elastic polyurethane foam sometimes referred to as memory foam), another type of foam, a conventional mattress, a box spring, a fluid bladder, a straw-filled pad, a feather-filled pad, a sawdust-filled pad, a spring-based pad, and/or another material that offers flexibility and/or softness. A top side 22 of the bottom layer 14 can partially define a recess 24 sized to receive the sensing layer 18. The recess 24 can have a depth less than a height of the sensing layer 18 when inflated to a normal pressure as shown in FIG. 2. The recess 24 can have one open end 26 at a foot of the mattress 12 as shown in FIG. 1. The open end 26 can allow a cord, hose, or other structure to easily access the sensing layer 18, and the open end 26 can be on a different side of the mattress 12 than shown in FIGS. 1 and 2.

The top padding layer 20 can be a comfort layer, which can be softer (i.e., less firm) than the bottom padding layer 14. The top layer 20 can include high density foam (e.g., memory foam), another type of foam, a conventional mattress, a fluid bladder, a straw-filled pad, a feather-filled pad, a sawdust-filled pad, a spring-based pad, and/or another material that is offers flexibility and/or softness. A bottom side 28 can partially define the recess 24. Alternatively, the recess 26 can be entirely defined by just one of the bottom layer 16 and the top layer 20. Also, depending on the thickness of the air bladder 18 and the firmness of the bottom and top layers 16 and 20, among other considerations, the bladder 18 can fit between layers 16 and 20 without the need for the recess 26.

Figure 3:
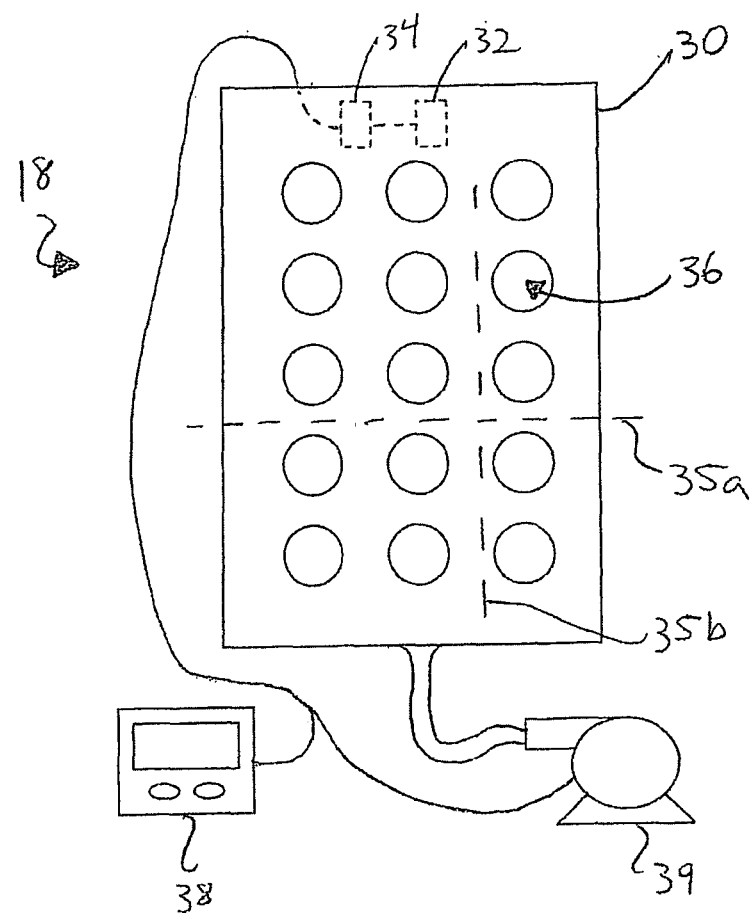
FIG. 3 is a plan view the sensing layer of FIG. 1.

The sensing layer 18 as shown in FIG. 3 includes a fluid bladder 30, a pressure sensor 32 configured to sense a fluid pressure within the fluid bladder 30, and a controller 34. The sensing layer 18 is also shown coupled to a control unit 38 and a pump 39. However, instead of using the pump 39 to inflate the bladder 30, another inflation mechanism can be provided. For example, the bladder 30 can be self-inflating by including a foam or other material within the bladder 30. As another example, compressed gas (e.g., compressed air or $CO_2$) can be used to inflate the bladder 30. Also, as is explained below in greater detail, the pressure sensor 32 can detect pressure changes caused by, for example, a pulse and/or breath of a user on the mattress 14, and the controller 34 can determine the user's heart rate, respiration rate, and/or other vital signs based on the detected pressure changes.

The fluid bladder 30 can hold air or another fluid, such as water, gel, another gas, or a combination thereof. The fluid bladder 30 can be sized to extend over a large portion of the top side 22 of the bottom layer 16, such as substantially the entire top side 22 of the bottom layer 16 as shown in FIG. 1. Alternatively, the bladder 30 can cover a smaller area of the top side 22 than as shown, such as an area of the top side 22 above which the torso of a user is expected to be positioned. Thus, the size of the fluid bladder 30 can allow the fluid bladder 30 to sense pressure changes over a wide range of positions of the user on the mattress 14. That is, even if the pressure sensor 32 is far from a source of a pressure change (e.g., a beating heart or inhaling or exhaling lungs of the user), the pressure change can create a wave within the bladder 30 propagating the pressure change to the sensor 32.

Also, the bladder 30 can be shaped to achieve a balance between allowing air to pass across the bladder 30 and providing the bladder 30 with a large area such that pressure changes are not dampened too greatly before reaching the bladder 30. Allowing air to pass across the bladder 30 can be beneficial for multiple reasons. First, passing air can dissipate heat from the top layer 20, thereby reducing a feeling of warmth common among foam mattresses. Second, passing air can remove moisture, thereby reducing the likelihood of mold growth within the mattress 14.

To achieve this balance, the bladder 30 as shown in FIG. 3 defines a plurality of apertures 36 arranged in a grid pattern. The apertures 36 can allow heat and moisture to pass across the bladder 30. Due to the arrangement of the apertures 36, the bladder 30 defines transverse and lengthwise paths shown, respectively, by lines 35a and 35b in FIG. 3. Waves caused by pressure changes input to the top layer 20 can propagate along the paths 35a and 35b to the sensor 32. Thus, the bladder 30 as shown in FIG. 3 can both allow moisture to pass between the layers 16 and 20 and can prevent pressure input to the top layer 20 from being dampened before reaching the sensor 32.

Figure 4:
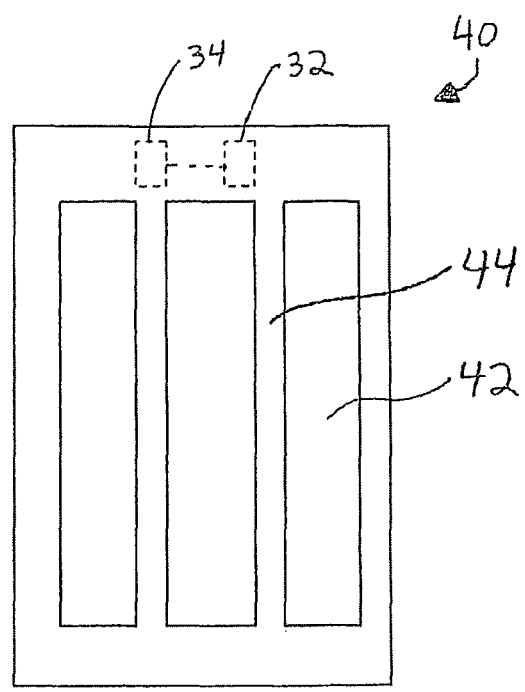
FIG. 4 is a plan view of another example of a sensing layer.

However, the bladder 30 can have a different shape from illustrated while still achieving similar functionality. For example, FIG. 4 shows a bladder 40 including longitudinal slots 42 for allowing moisture to pass the bladder 40. The bladder 40 also includes longitudinal connectors 44 for allowing waves to propagate to the sensor 32 in the bladder 40. The sizes of the slots 42 and connectors 44 can be a trade off between providing a large area for the passage of moisture and providing the bladder 40 with a large area to prevent pressure changes from being dampened before reaching the bladder 40. As another example in which the shape of the bladder 30 can different from as shown in FIG. 3, the fluid bladder 30 can include multiple discrete compartments, in which case each compartment can include one of the pressure sensors 32. For example, if the mattress 14 is large enough for two users, the mattress 14 can include two discrete compartments, each including its own sensor 32, for separately detecting the vital signs of the two users. However, the pressure detected by a single sensor 32 can indicate vital signs of multiple users, and the controller 34 can perform a pattern recognition algorithm or other calculation to determine the users' respective vital signs as explained in more detail below.

As shown in FIG. 6, the sensing layer 18 can be subject to a shearing force is a lateral force applied to the top padding layer 20. As a result, the sensing layer 18 can be deformed to the shape shown in phantom at 18'. The height 31 of the fluid bladder 30 can be great enough such that when the sensing layer 18 undergoes an expected amount of deformation, the top of the sensing layer 18 does not contact the bottom of the sensing layer 18. Contact between the top and bottom of the sensing layer 18 can allow force to be transmitted directly from the top padding layer 20 to the bottom padding layer 16, in which case the pressure sensor 32 may not accurately detect pressure changes in the fluid bladder 30. The height 31 can also be based on the expected weight of the top padding layer 20 and any users that rest thereon, as well as the expected pressure within the fluid bladder 30. Under normal conditions (e.g., a normal user weight and a normal top layer 20 weight), the fluid bladder 30 portion of the sensing layer 18 can have an approximately 1.0" height.

As mentioned above, the pressure sensor 32 can be configured to sense a fluid pressure within the fluid bladder 30. For example, the pressure sensor 32 can be inside the bladder 30. As another example, the pressure sensor can be in a portion of the pump 39 in fluid communication with the bladder 30, and thus in a portion of the pump 39 having a pressure corresponding to a pressure in the bladder 30. The sensor 32 can include a semiconductor pressure sensor or another type of pressure sensor. Additionally, other types of sensors, such as a temperature sensor, can also be included. The sensor 22 can output a pressure signal $\alpha$ to the controller 34.

Further, the pressure signal a can indicate the whether or not a person is lying on the bladder 30, the heart rate of a person lying on the bladder 30, the respiration rate of a person lying on the bladder 30, other movement (e.g., rolling or limb movement) of a person lying on the bladder 30, the temperature of the fluid in the bladder 30, and vital signs because all these can be factors of the pressure within the fluid bladder 30.

The controller 34, which can include a memory and a CPU for executing a program stored on the memory, can control the pump 39 to produce pressurized air. For example, the controller 34 can control the pump 39 in response to the pressure signal a such as by instructing the pump 39 to inflate the bladder 30 when the controller 34 determines the pressure in the bladder 30 is below a set amount. While the controller 34 is shown as inside the bladder 30, the controller 34 can alternatively be part of the control unit 38 or otherwise located outside the bladder 30. The controller 34 can be hard-wired to the sensor 32 and/or pump 39, in wireless communication with the sensor 32 and/or pump 39 using, e.g., a standard wireless protocol (IEEE 802.11, Bluetooth, etc.), or the controller 34 can communicate with the sensor 32 and/or pump 39 in another way.

Additionally, the controller 34 can analyze the pressure signal a to determine a heart rate, respiration rate, and/or other vital signs of a user lying or sitting on the mattress 12. As explained above, when a user lies on the top layer 20, each of the user's heart beats and breaths can create a force on the top layer 20 that is transmitted to the bladder 30. As a result of the force input to the bladder 30 from a heart beat or breath, a wave can propagate through the bladder 30 to the sensor 32. The sensor 32 can detect the wave, and the pressure signal a output by the sensor 32 can thus indicate a heart rate or respiratory rate of a user. As a result, the bladder 30 can prevent waves from being dampened by foam prior to reaching the sensor 32.

To overcome a DC offset in the pressure signal $\alpha$, the pressure signal $\alpha$ can pass through a circuit splitting the signal into a DC coupled path and an AC coupled path, and the AC coupled path can be amplified and filtered. The controller 34 can perform a pattern recognition algorithm or other calculation based on the amplified and filtered pressure signal $\alpha$ to determine the user's heart rate and respiratory rate. For example, the algorithm or calculation can be based on assumptions that a heart rate portion of the signal $\alpha$ has a frequency in the range of 0.5-4.0 Hz and that a respiration rate portion of the signal α has a frequency in the range of the range of less than 1 Hz. The controller 34 can also be configured to determine other characteristics of a user based on the pressure signal α, such as blood pressure, tossing and turning movements, rolling movements, limb movements, weight, or the identity of the user. Further, the controller 34 can receive signals from other sensors (e.g., a temperature sensor). The controller 34 can output a status signal β indicating the characteristics of the user (e.g., heart rate and respiratory rate) to the control unit 38.

The control unit 38 can include a transmitter, a display screen, and controls. The transmitter can relay the status signal β to a database or other source. The transmitter can be a wireless transmitter operating using a standard wireless protocol (e.g., IEEE 802.11, RF, Bluetooth, or 3G), though the transmitter can alternatively be hardwired to the remote source using a phone line, Ethernet line, or other connection. As a result, the database can store sleep information produced as a result of the status signal β, and the user can be alerted to sleep issues based on long-term sleep trends or provided with other communications regarding the user's sleep (e.g., an alarm warning of apnea), fitness level, cardiovascular condition, or other health information.

The display screen can display information relayed in the status signal β, such as a sleep score based on the user's heart rate, respiratory rate, amount of time spend in REM sleep, total time in bed, and other considerations.

The controls can be used to control the operation of the sensor 32 and/or controller 34. For example, the controls can be used to increase the pressure in the bladder 30, instruct the sensor 32 and/or controller 34 to operative in a privacy mode in which data is not detected, retained, displayed, transmitted, and/or analyzed, or to communicate with the database to obtain sleep information (e.g., sleep trends, sleep scores from previous nights, sleeping tips). The database can alternatively or additionally be accessible using a computer, e.g., via the internet.

The pump 39 can be a rotary type pump or another type of pump. The pump 39 can be fluidly coupled to the bladder 30 via a hose. However, the pump 39 can alternatively be integral with the mattress 14 such that a hose is not necessary.

Figure 5:
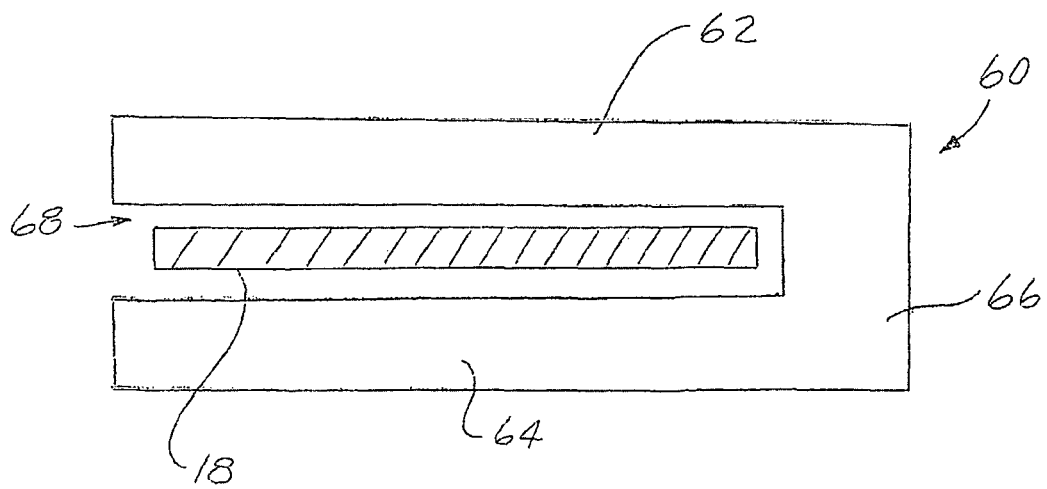
FIG. 5 is a side view of another example of a mattress including a sensing layer.

The mattress 14 can have a different configuration from as shown in FIGS. 1-2. As such, while the bottom layer 16, sensing layer 18, and top layer 20 are shown as being discrete structures, alternative configurations are possible. For example, FIG. 5 illustrates a foam mattress 60 including a top portion 62 and a bottom portion 64 connected by a linking portion 66. The mattress 60 defines an envelop 68 for receiving the sensing layer 18. As additional examples, the sensing layer 18 can be sealed within the mattress 14 during the manufacture of the mattress 14, or the sensing layer 18 and top layer 20 can be integral. Also, in another example, the bladder 30 can be positioned between a foundation (e.g., the frame 12) and the bottom layer 16 of the mattress 14.

While the invention has been described in connection with what is presently considered to be the most practical example, it is to be understood that the invention is not to be limited to the disclosed example but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A sleep monitoring system comprising:
a mattress sized for use in a bed frame comprising:
a first padding layer sized to fit to the bed frame; and
a sensing layer sized smaller than and positioned below the first padding layer, the sensing layer comprising a fluid bladder and a sensor positioned within the fluid bladder and in fluid communication with the fluid bladder, the sensor configured to detect waves propagated within the fluid bladder;
an inflation mechanism in fluid communication with the fluid; and
a controller located within the mattress and configured to:
receive signals from the sensor;
analyze the signals using pattern recognition to differentiate the signals based on frequency;
convert analysis results to vital signs of a subject on the mattress; and
output the vital signs of the subject to a control unit, wherein the fluid bladder defines at least one aperture extending from a first surface of the fluid bladder adjacent the first padding layer to a second surface of the fluid bladder opposite the first surface configured to provide a pass-through for fluids.

2. The sleep monitoring system of claim 1, wherein the at least one aperture includes a plurality of apertures in a grid formation.

3. The sleep monitoring system of claim 1, wherein the at least one aperture includes multiple longitudinally extending slots spaced across a width of the fluid bladder and having a length less than a length of the fluid bladder.

4. The sleep monitoring system of claim 3, wherein the multiple longitudinally extending slots define longitudinally extending fluid pathways extending the length of the fluid bladder and in open communication with each other.

5. The sleep monitoring system of claim 4, wherein the sensor is in fluid communication with at least one of the pathways.

6. A sleep monitoring system comprising:
a mattress sized for use in a bed frame comprising:
a first padding layer sized to fit to the bed frame; and
a sensing layer sized smaller than and positioned below the first padding layer, the sensing layer comprising a fluid bladder and a sensor positioned within the fluid bladder and in fluid communication with the fluid bladder, the sensor configured to detect waves propagated within the fluid bladder;
an inflation mechanism in fluid communication with the fluid; and
a controller located within the mattress and configured to:
receive signals from the sensor;
analyze the signals using pattern recognition to differentiate the signals based on frequency;
convert analysis results to vital signs of a subject on the mattress; and
output the vital signs of the subject to a control unit, wherein the fluid bladder includes connectors extending between a top side of the fluid bladder upon which the first padding layer rests and a bottom side of the fluid bladder, the connectors at least partially defining pathways along which the waves move toward the sensor.

7. The sleep monitoring system of claim 6, wherein the control unit is operative to at least one of display the vital sign, produce an alarm when warranted by the vital sign, and control at least one of the sensor and the controller.

8. The sleep monitoring system of claim 6, further comprising a transmitter in communication with a database.

9. The sleep monitoring system of claim 6, wherein the inflation mechanism is a pump integral with the mattress, the controller further configured to operate the pump to maintain a predetermined pressure within the fluid bladder.

10. The sleep monitoring system of claim 6, wherein the first padding layer has a surface in which a recess is formed, the recess configured to receive at least a portion of the bladder to reduce an overall height of the mattress.

11. The sleep monitoring system of claim 6, wherein the controller is further configured to differentiate the signals based on strength and convert analysis results to monitor movement of the subject on the mattress.

12. The sleep monitoring system of claim 6, wherein the controller is further configured to identify the subject on the mattress based on the vital signs associated with the subject, wherein the vital signs include heart rate and respiration rate.

13. The sleep monitoring system of claim 6, wherein a firmness of the second padding layer is greater than a firmness of the first padding layer.

14. The sleep monitoring system of claim 6, wherein the mattress further comprises a second padding layer, with the sensing layer sandwiched between the first padding layer and the second padding layer; and an opening in an end of one or both of the first padding layer and the second padding layer to house the inflation mechanism and access the sensing layer.

15. The sleep monitoring system of claim 14, wherein the first padding layer has a surface in which a recess is formed and the second padding layer has a surface with a corresponding recess, the recess and the corresponding recess configured receive and enclose the bladder to reduce an overall height of the mattress.

16. A mattress for determining a vital sign of a person lying thereon, the mattress comprising:

a first foam layer;

a second foam layer;

a fluid bladder between the first and second foam layers, the fluid bladder defining at least one aperture extending between a top side of the fluid bladder that the first foam layer rests on and a bottom side that rests on the second foam layer, the at least one aperture configured as a pass-through for fluid; and a sensor in fluid communication with the fluid bladder, the sensor configured to detect waves propagated within the fluid bladder; and a controller configured to:

receive signals from the sensor; and analyze the signals using pattern recognition to differentiate the signals based on strength and frequency, with one strength and frequency associated with a heart rate, a second strength and frequency associated with a respiration rate, and a third strength and frequency associated with limb movement.

17. The mattress of claim 16, wherein the first foam layer has a surface in which a recess is formed and the second foam layer has a surface with a corresponding recess, the recess and the corresponding recess configured receive and enclose the fluid bladder to reduce an overall height of the mattress.

18. A sleep monitoring system comprising:

a fluid bladder;

a sensor in fluid communication with the fluid bladder and operative to detect waves propagated within the fluid bladder; and a controller configured to:

receive signals from the sensor; and analyze the signals using pattern recognition to differentiate the signals based on strength and frequency, with one strength and frequency associated with a heart rate, a second strength and frequency associated with a respiration rate, and a third strength and frequency associated with limb movement, wherein the fluid bladder defines at least one aperture extending from a first surface of the fluid bladder to a second surface of the fluid bladder opposite the first surface configured to provide a pass-through for fluids.

19. The sleep monitoring system of claim 18, wherein the controller is further configured to identify a subject on the fluid bladder based on the heart rate and respiration rate.

* * * * *